(12) United States Patent
Bruccoleri

(10) Patent No.: US 9,333,183 B2
(45) Date of Patent: May 10, 2016

(54) SELF-ASSEMBLING POLYPHENOL-QUINONOID POLYMER DERIVATIVES AND USES THEREOF

(75) Inventor: Aldo Bruccoleri, Lacombe (CA)

(73) Assignee: ABRA PHARMACEUTICAL SARL, Lausanne (CH)

( * ) Notice: Subject to any disclaimer, the term of this patent is extended or adjusted under 35 U.S.C. 154(b) by 0 days.

(21) Appl. No.: 13/883,372

(22) PCT Filed: Nov. 3, 2011

(86) PCT No.: PCT/IB2011/054903
§ 371 (c)(1),
(2), (4) Date: May 3, 2013

(87) PCT Pub. No.: WO2012/059884
PCT Pub. Date: May 10, 2012

(65) Prior Publication Data
US 2013/0231396 A1    Sep. 5, 2013

Related U.S. Application Data

(60) Provisional application No. 61/410,068, filed on Nov. 4, 2010.

(30) Foreign Application Priority Data

Jan. 11, 2011   (EP) .................... 11150561

(51) Int. Cl.
| | |
|---|---|
| A61K 31/09 | (2006.01) |
| A61K 31/085 | (2006.01) |
| C08G 65/38 | (2006.01) |
| C07C 43/295 | (2006.01) |
| C07C 41/01 | (2006.01) |

(52) U.S. Cl.
CPC .............. *A61K 31/09* (2013.01); *A61K 31/085* (2013.01); *C07C 43/295* (2013.01); *C08G 65/38* (2013.01); *C07C 41/01* (2013.01)

(58) Field of Classification Search
None
See application file for complete search history.

(56) References Cited

U.S. PATENT DOCUMENTS

2002/0048561 A1    4/2002  Laub

FOREIGN PATENT DOCUMENTS

| EP | 0537430 | 4/1993 |
|---|---|---|
| RU | 2224737 C2 | 2/2004 |
| WO | WO 98/34606 | 8/1998 |

OTHER PUBLICATIONS

DeFrancesco et al., "Challenges and successes in developing new therapies for hepatitis C", Nature, 436(18), pp. 953-960 (2005).*
Database CA [Online] Chemical Abstracts Service, Accession No. 1953:41674, Tomita, M. et al. "Antibacterial activity of some organic compounds in vitro. VI. Antibacterial activity of diphenyl ethers and related compounds on *Mycobacterium tuberculosis*, Micrococcus pyogenes var. aureus, and *Escherichia coli*" Apr. 22, 2001, XP-002669942, pp. 1-2.

(Continued)

*Primary Examiner* — Bethany Barham
*Assistant Examiner* — Barbara Frazier
(74) *Attorney, Agent, or Firm* — Saliwanchik, Lloyd & Eisenschenk

(57) ABSTRACT

The invention relates to novel polyphenol-quinonoid polymer derivatives, methods of synthesizing, compositions and uses thereof. In particular, the invention relates to polyphenol-quinonoid polymer derivatives useful in the treatment of viral infections, notably conditions caused by retroviruses such as human immunodeficiency virus (HIV).

1 Claim, 7 Drawing Sheets

(56) References Cited

OTHER PUBLICATIONS

Database CA [Online] Chemical Abstracts Service, Accession No. 2004:242695, Alkatseva, N. et al. "A preparation of polyoxyphenylene ethers with combined antioxidant and antihypoxic properties" 2004, XP-002625736, p. 1.

Ungnade, H. E. et al. "2,3',5-Trihydroxydiphenyl Ether" *The Journal of Organic Chemistry*, May 17, 1949, pp. 911-914, vol. 14. No. 5.

Ungnade, H. E. et al. "Phenoxyquinones. III. 2-(Hydroxyphenoxy)-*p*-Benzo-Quinones" *The Journal of Organic Chemistry*, Jul. 3, 1950, pp. 70-72. vol. 16. No. 1.

Loya, S. et al. "Peyssonols A and B, Two Novel Inhibitors of the Reverse Transcriptases of Human Immunodeficiency Virus Types 1 and 2" *Achieves of Biochemistry and Biophysics*, Feb. 1, 1995, pp. 789-796, vol. 316, No. 2.

Lucas, G. "Antiretroviral adherence, drug resistance, viral fitness and HIV disease progression: a tangled web is woven" *Journal of Antimicrobial Chemotherapy*, 2005, pp. 413-416, vol. 55.

Li. F. et al. "HIV-1 assembly and budding as targets for drug discovery" *Curr. Opin. Investig. Drugs.*, Feb. 2005, pp. 148-154, vol. 6. No. 2. Abstract Only.

Schaeffer, D. J. et al. "Anti-HIV Activity of Extracts and Compounds from Algae and Cyanobacteria" *Ecotoxicology and Environmental Safety*, 2000, pp. 208-227, vol. 45.

Soares, A. M. et al. "Chemical modifications of phospholipases $A_2$ from snake venoms: effects on catalytic and pharmacological properties" *Toxicon*, pp. 855-868, vol. 42.

Schneider, J. et al. "Inhibition of HIV-1 in Cell Culture by Synthetic Humate Analogues Derived from Hydroquinone: Mechanism of Inhibition" *Virology*, 1996, pp. 389-395, vol. 218.

Leenheer, J. et al. "Aquatic Organic Matter" *Environmental Science & Technology*, Jan. 1, 2003, pp. 18A-26A.

Laurberg, P. et al. "Humic substances in drinking water and the epidemiology of thyroid disease" *BioFactors*, 2003, pp. 145-153, vol. 19.

Bruccoleri, A. "The Photophysics and Photochemistry of Fulvic Acid" *The University of Calgary*, 2000, Ph.D. Thesis, see pp. 92-113.

Bruccoleri, A. G. et al. "Molecular Modeling of Humic Structures" *Humic substances—Structures, models and functions: Cambridge, Royal Society of Chemistry*, 2001, p. 193-208.

Gamble, D.S. et al. "Chemical Stoichiometry and Molecular Level Mechanisms as Support for Future Predictive Engineering Calculations" *Chapter 3, eds. I. V. Perminova, N. Herkom, and P. Baveye. Use of humic substances to remediate polluted environments: From theory to practice. NATO Science Series, Kluwer Academic Publisher*, Dordrecht, 2005, pp. 53-79.

Ariese. F. et al. "Comparison of Laurentian Fulvic Acid luminescence with that of the hydroquinone/quinone model system: Evidence from low temperature fluorescence studies and EPR spectroscopy" *Aquatic Sciences*, 2004, pp. 86-94, vol. 66.

Bruccoleri, A. et al. "Evaluation of Primary Photoproduct Quantum Yields in Fulvic Acid" Environmental Science & Technology, 1993, pp. 889-894, vol. 27.

Wainberg, M. et al. "Changing Patterns in the Selection of Viral Mutations among Patients Receiving Nucleoside and Nucleotide Drug Combinations Directed against Human Immunodeficiency Virus Type 1 Reverse Transcriptase" *Antimicrobial Agents and Chemotherapy*, May 2005, pp. 1671-1678, vol. 49, No. 5.

Salama, N. N. et al. "Tight junction modulation and its relationship to drug delivery" *Advanced Drug Delivery Reviews*, 2006, pp. 15-28, vol. 58.

Ralph, S. et al. "NMR Database of Lignin and Cell Wall Model Compounds" *US Forest products Laboratory, US Dairy Forage Research Center and USDA Agriculture Service*, 2004, pp. 1-449.

\* cited by examiner

A

B

C

A

B

C

D

A

B

SELF-ASSEMBLING POLYPHENOL-QUINONOID POLYMER DERIVATIVES AND USES THEREOF

CROSS-REFERENCE TO RELATED APPLICATIONS

This application is the U.S. national stage application of International Patent Application No. PCT/IB2011/054903, filed Nov. 3, 2011, which claims the benefit of U.S. Provisional Patent Application No. 61/410,068, filed Nov. 4, 2010.

FIELD OF THE INVENTION

The present invention relates to polyphenol-quinonoid polymer derivatives and methods of synthesizing thereof. In particular, the invention relates to polyphenol-quinonoid polymer derivatives useful in the treatment retroviral infections, notably conditions caused by retroviruses such as human immunodeficiency virus (HIV). In particular, the invention relates to polyphenol-quinonoid polymer derivatives useful as multifunctional antimicrobial agents, in particular as antimicrobial dyes or stains.

BACKGROUND OF INVENTION

High virus burden together with depletion of $CD4^+$ T cells is correlated with the progression of human immunodeficiency virus (HIV)-1 infection towards acquired immunodeficiency syndrome (AIDS), which is sustained by high virus replication and ongoing infection of target cells. HIV treatment is presently achieved through highly active antiretroviral therapy (HAART), which aims to maximize life expectancy while maintaining quality of life and minimizing drug toxicity. However, lifelong treatment with HAART is needed to maintain suppression of the viral load below 50 copies/ml because a cure is not possible with currently available agents (Lucas et al., 2005, *J. Antimicrob. Chemother.*, 55, 413-6). Further, growing drug resistance seen in HIV/AIDS patients subjected to therapy and newly acquired HIV-1 infections underscores the requirement for new antiretroviral agents, as well as increasing the robustness of existing therapies.

For rational drug design to inhibit retrovirus infections, different stages of the virus replication cycle have been targeted (Li et al., 2005, *Curr. Opin. Investig. Drugs*, 6, 148-54). These steps include virus penetration, un-coating and/or virus adsorption to its cellular receptor, transcription of the viral RNA genome to proviral DNA (reverse transcription), trans-activation of viral mRNA transcription and translation, assembly process and virus release (Li et al., 2005, above), although reverse transcriptase (RT) inhibitors have been proven to be the most effective agents to date (Wainberg et al., 2005, *Antivir. Ther.*, 10, 13-28). However, emergence of drug resistance in patients treated with reverse transcriptase inhibitors is a major limitation of antiviral therapy (Salama et al., 2006, *Infect. Disord. Drug Targets*, 6, 107-19).

Among natural products with anti-HIV-1 properties, several agents have been isolated from algae and cyanobacteria (Schaeffer et al., 2000, *Ecotoxicol. Environ. Sal*, 45, 208-27), snake venom (Soares et al., 2003, *Toxicon*, 42, 855-68) and humics (Schneider et al., 1996, *Virology*, 218, 389-95). Humics are a soil- and water-derived heterogeneous mixture of polydisperse polymers in the molecular weight range from a few hundred to tens of thousands that have been studied for their antiretroviral properties (Leenheer et al., 2003, *Environ. Sci. Technol.*, 37, 18A-26A; Laurberg et al., 2003, *Biofactors*, 19, 145-53).

Humic polyphenols and quinonoids represent a fraction of humic substances presenting complex binding interactions, self-assembling interactions, reduction/oxidation interactions and free-radical quenching antioxidant behavior (Bruccoleri et al., 2000, *University of Calgary, PhD Thesis*, p. 92-113; Bruccoleri et al., 2001, *Molecular modeling of humic substances*, in Ghabbour, E. A. and Davies, Geoffrey, eds., *Humic substances—Structures, models and functions: Cambridge, Royal Society of Chemistry*, p. 193-208; Gamble et al., 2005, *Chemical stoichiometry and molecular level mechanisms as support for future predictive engineering*. Chapter 6 In, eds. I. V. Perminova, N. Herkorn, and P. Baveye. *Use of humic substances to remediate polluted environments: From theory to practice. NATO Science Series*, Kluwer Academic Publisher, Dordrecht).

Two sesquiterpene hydroquinones, peyssonol A and peyssonol B, of the Red Sea algae *Peyssonelia* sp., have been shown to be potent inhibitors of HIV-1 and HIV-2 RT by acting as non-competitive RT inhibitors and repressors of HIV-1 replication (Loya et al., 1995, *Arch. Biochem. Biophys.*, 316, 789-96).

A stable synthetic polymer with low toxicity and mutagenicity, HS-1500, synthesised by oxidation of hydroquinone at high pH, was found to inhibit HIV-1 in vitro, putatively through a hydrophobic/ionic interaction of HS-1500 with the V3 loop of the HIV-1 gp120 envelope protein (Schneider et al., 1996, above). Hydroquinones show limited cytotoxicity and carcinogenicity although bone marrow micronuclei have been reported. Further, epidemiological studies with hydroquinones have demonstrated lower death rates and reduced cancer incidences among individuals employed in the production of hydroquinones.

Due to the high ability of the virus to present mutational resistance and the emergence of drug-resistant strains of virus, there is a crucial need for the discovery and development of alternative anti-HIV agents, in particular active in inhibiting RT activity.

With rising concern about the spread of superbugs, healthcare trusts are increasingly looking to find new antimicrobial agents. Textile materials and clothing are known to be susceptible to microbial attack, by providing large surface areas and absorbing moisture required for microbial growth. Therefore, antimicrobial agents which can dye or stain textile or other materials have attracted significant attention in recent years because of the increasing concern on cross-contamination of diseases in public places and hospitals (Sun, 2005, *J. Chem. Educ.*, 82, 60-64). In order to reduce rates of disease transmission and infection in hospitals, there is an increased interest in finding new antimicrobial agents with dye properties which can be used and incorporated into textiles for healthcare workers and patients and/or paint pigments for surfaces used in the healthcare venue.

SUMMARY OF THE INVENTION

The invention relates to the finding of novel self-assembly polyphenol-quinonoid polymer derivatives and mixtures thereof which exhibit both anti-HIV-1 and anti-feline immunodeficiency virus (FIV) properties in primary and immortalized cell cultures, as well as in an established in vivo model. Those antiviral properties are observed at low $IC_{50}$ values and are characterized by a reduction of viral reverse transcriptase levels, while also suppressing HIV-induced syncytia formation. The polyphenol-quinonoid polymer derivatives mixtures show activity in suppressing HIV-1 and FIV replication and infectivity through inhibition of RT activity, while exhibiting a minimal cytotoxicity. The invention relates to the finding that novel self-assembly polyphenol-quinonoid polymer derivatives according to the invention exhibit antimicrobial properties.

The present invention is further related to the finding of novel methods of synthesizing a derivative polyphenol-quinonoid polymer derivative, in particular by a single autocatalytic free radical reaction. The invention further relates to pharmaceutical compositions comprising at least one polyphenol-quinonoid polymer derivative according to the invention, uses and methods of use thereof. In particular, the methods, uses, formulations and compositions according to the invention are useful in the prevention and treatment of a condition or disorder caused by a retrovirus. In addition, the methods, uses, formulations and compositions according to the invention are useful in the prevention and treatment of bacterial infections.

A first aspect of the invention provides a mixture of polyphenol-quinonoid polymer derivatives according to Formula (I).

A second aspect of the invention provides mixture of polyphenol-quinonoid polymer derivatives according to the invention for use as a medicament.

A third aspect of the invention provides a pharmaceutical formulation comprising at least one mixture of polyphenol-quinonoid polymer derivatives according to the invention and at least one pharmaceutically acceptable carrier.

A fourth aspect of the invention provides a formulation according the invention for use as a medicament.

A fifth aspect of the invention provides a process of preparation of a polyphenol-quinonoid polymer derivative or a mixture thereof.

A sixth aspect of the invention provides a polyphenol-quinonoid polymer derivative or a mixture thereof obtainable by a process according to the invention.

A seventh aspect of the invention provides a mixture of polyphenol-quinonoid polymer derivatives according to the invention or a formulation thereof for the prevention and/or treatment or repression of a disease or disorder caused by viral infections in particular a condition or disorder caused by a retrovirus.

An eighth aspect of the invention provides a mixture of polyphenol-quinonoid polymer derivatives according to the invention or a formulation thereof for the prevention and/or treatment or repression of a disease or disorder caused by bacterial infections.

A ninth aspect of the invention provides a use of a mixture of polyphenol-quinonoid polymer derivatives according the invention or a formulation thereof for the preparation of a pharmaceutical composition for the prevention and/or treatment or repression of a disease or disorder caused by viral condition or disorder caused by a retrovirus.

A tenth aspect of the invention provides a use of a mixture of polyphenol-quinonoid polymer derivatives according the invention or a formulation thereof for the preparation of a pharmaceutical composition for the prevention and/or treatment or repression of a disease or disorder caused by bacterial infections.

An eleventh aspect of the invention provides a method of preventing and/or treating or repressing a disease or disorder caused by viral condition or disorder caused by a retrovirus, said method comprising administering in a subject in need thereof a therapeutically effective amount of a mixture of polyphenol-quinonoid polymer derivatives according the invention or a formulation thereof.

A twelfth aspect of the invention provides a method for inhibiting reverse transcriptase in a host infected with a retrovirus, in particular HIV-1, comprising administering a therapeutically effective amount of a mixture of polyphenol-quinonoid polymer derivatives according to the invention or a formulation thereof to a host in need thereof.

A thirteenth aspect of the invention provides a method of eliminating virus infectivity in a blood product, said method comprising contacting said blood product with an effective amount of a mixture of polyphenol-quinonoid polymer derivatives according to the invention or a formulation thereof.

A fourteenth aspect of the invention provides an article coated with an effective amount of a mixture of polyphenol-quinonoid polymer derivatives according to the invention or a formulation thereof.

A fifteenth aspect of the invention provides a method of preventing and/or treating or repressing a disease or disorder caused by bacterial infections, said method comprising administering in a subject in need thereof a therapeutically effective amount of a mixture of polyphenol-quinonoid polymer derivatives according the invention or a formulation thereof.

A sixteenth aspect of the invention provides a method of preventing a disease caused by bacterial infections comprising the coating of an effective amount of a mixture of polyphenol-quinonoid polymer derivatives according the invention on a surface of a material used in healthcare such as in surgery or intensive care (such as textile for healthcare, paint for healthcare in healthcare venue, tubings etc. . . . ).

A seventeenth aspect of the invention provides a use of a mixture of polyphenol-quinonoid polymer derivatives according the invention as a multifunctional antibacterial agent or for the preparation of a multifunctional antibacterial composition.

An eighteenth aspect of the invention provides a use of a mixture of polyphenol-quinonoid polymer derivatives according the invention as a staining agent.

A nineteenth aspect of the invention provides a straining composition comprising a mixture of polyphenol-quinonoid polymer derivatives according the invention.

DETAILED DESCRIPTION

Figure 1:
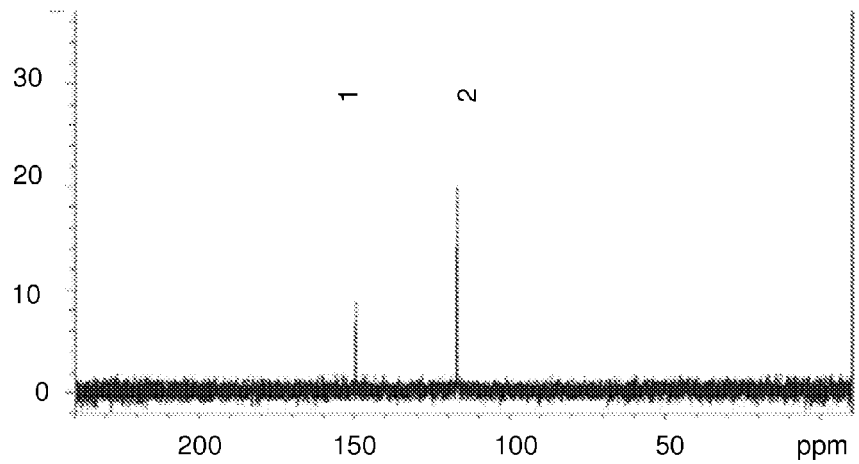
FIG. 1: Characterization and cytotoxicity of a polyphenol-quinonoid polymer according to the invention. A: $^{13}$C-NMR spectra showing two relatively narrow bands centered near 149 ppm (1) and 117 ppm (2) for all fractions of the "polymer-1" mixture obtained as described in Example 1; B: Percentage of cytotoxicity of polyphenol-quinonoid polymer according to the invention on Peripheral Blood Mononuclear Cells (PBMCs) at increasing concentrations, as measured by trypan-blue dye exclusion at 6 and 24 h post-treatment as described in Example 1; C: Percentage of cytotoxicity of polyphenol-quinonoid polymer according to the invention ("polymer 1") versus control polymer (polymer 2) and controls on PBMCs at increasing concentrations of polymer, as measured by trypan-blue dye exclusion at 24 h post-treatment as described in Example 1.
Figure 1:
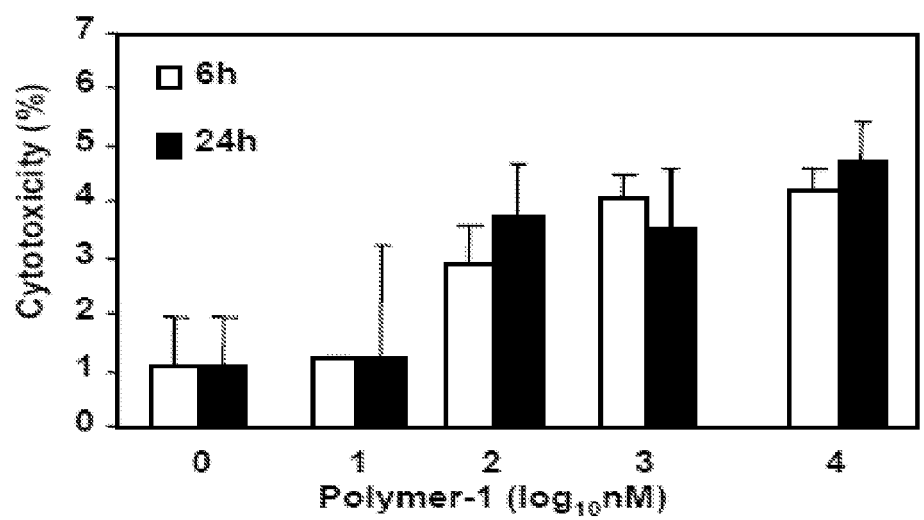
Figure 1:
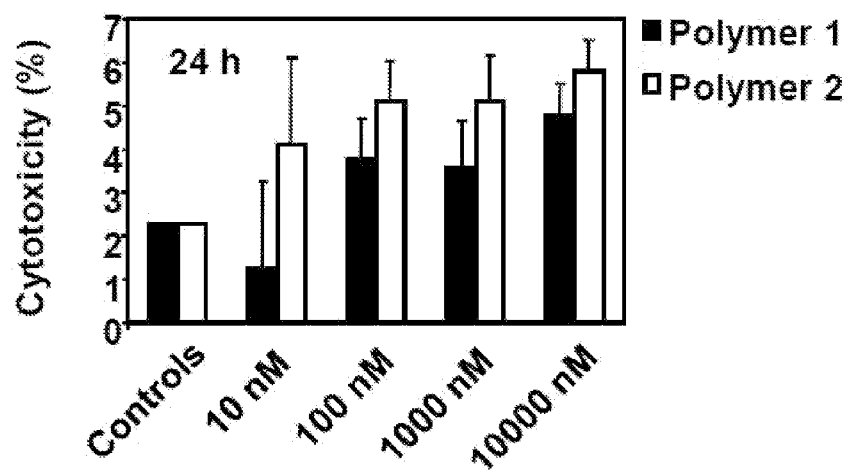

The term "polymer," as used herein, is given its ordinary meaning as used in the art, i.e., a molecular structure comprising one or more repeating units (monomers), connected by covalent bonds. The term "polymer" comprises a mixture of polymers comprising different numbers of repeating units.

As used herein, "treatment" and "treating" and the like generally mean obtaining a desired pharmacological and physiological effect. The term "treatment" as used herein covers any treatment of a disease in a mammal, particularly a human, and includes inhibiting the disease, i.e., arresting its development; or relieving the disease, i.e. causing regression of the disease and/or its symptoms or conditions such as lowering viral loads, decreasing viral replication and slowing disease progression. In a particular embodiment, a treatment according to the invention is useful for preventing the spread of retroviral, notably HIV infection. In a particular embodiment, a treatment according to the invention include inhibition of syncytia formation (multinucleated giant cells that are formed following the fusion of infected cells and are involved in the direct cell-to-cell infection). The term "human immunodeficiency virus" or "HIV" shall be used to describe human immunodeficiency viruses 1 (HIV-1).

The term "subject" as used herein refers to mammals. For examples, mammals contemplated by the present invention include human, primates, domesticated animals such as cats and the like.

The term "effective amount" as used herein refers to an amount of at least one polyphenol-quinonoid polymer or a pharmaceutical formulation thereof according to the invention that elicits the biological or medicinal response in a tissue, system, animal or human that is being sought. In one embodiment, the effective amount is a "therapeutically effective amount" for the alleviation of the symptoms of the disease or condition being treated. Typically, an effective amount can be used to inhibit HIV reverse transcriptase, or another enzyme required for HIV replication or infection, for treatment or prophylaxis of infection by HIV, or for treatment, prophylaxis of, or delay in the onset or progression of AIDS and/or diseases or conditions arising therefrom or associated therewith.

Typically, an effective amount can be used to inhibit Gram positive and Gram negative bacterial growth.

The term "disease cause by bacterial infection" comprises nosocomial infection such as pneumonitis, tuberculosis, pneumonia, cystic fibrosis, endocarditis, meningitis, external otitis, eye, bone, joint, gastrointestinal, urinary and skin diseases and disorders such as urinary tractus infections (e.g. cystitis).

The term "efficacy" of a treatment according to the invention can be measured based on changes in the course of a disease in response to a use or a method according to the invention.

The term "multifunctional antimicrobial" according to the invention refers to agents that present an antibacterial function and some dye-like or stain-like properties, such as staining, visible and fluorescent dye properties.

The term "staining" agent or composition refers to an agent or composition useful to stain potentially infected tissue samples for observation by microscopy or by fluorimetry.

The term "tissue sample" refers to infected bio-tissue being studied by health personnel or researchers under methods of fluoroscopy or microscopy.

The term "pharmaceutically acceptable prodrugs" refer to a compound that is metabolized in the host, for example hydrolyzed or oxidized, by either enzymatic action or by general acid or base solvolysis, to form an active ingredient.

The term "pharmaceutically acceptable salts" refer to refers to salts of the polymer derivatives according to the invention.

Polyphenol-Quinonoid Polymers According to the Invention

The polymers according to the invention are polyphenol-quinonoid polymers of Formula (I)

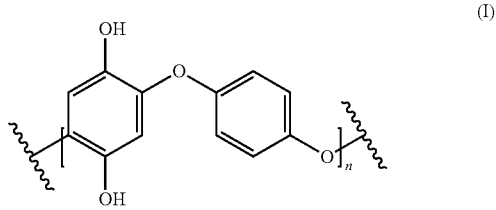

wherein n is an integer selected from 1 and 2. According to one aspect, pharmaceutically acceptable derivatives of the polymers according to the invention include optionally substituted polymers of Formula (I), in particular, polymers of Formula (II):

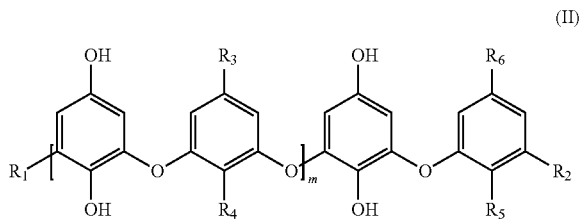

wherein $R^1$, $R^2$, $R^3$, $R^4$, $R^5$ and $R^6$ independently selected from H and OH, m is an integer selected from 0 and 1. In a particular embodiment, $R^1$ is H when m is 0.

A composition according to the invention comprises a mixture of polyphenol-quinonoid polymers of Formula (I), any pharmaceutically acceptable derivatives, any pharmaceutically acceptable salts or pro-drugs thereof presenting different n values, wherein the molecular weight of said mixture is lower or equal to 1000 grams per mole.

A composition according to the invention comprises a mixture of polyphenol-quinonoid polymers of Formula (I), any pharmaceutically acceptable salts or pro-drugs thereof presenting different n values, wherein the molecular weight of the said mixture is lower or equal to 1000 grams per mole.

According to one aspect of the invention, a polymer composition according to the invention the molecular weight of the said mixture is lower or equal to 1,000 grams per mole and higher than 266 g/mol.

According to another aspect of the invention, a polymer composition according to the invention the molecular weight of the said mixture is lower or equal to 266 g/mol.

According to one aspect of the invention, a polymer composition according to the invention is a polymer composition obtainable from a process according to the invention.

Compositions

The invention provides pharmaceutical or therapeutic agents as compositions and methods for treating a subject, preferably a mammalian subject, and most preferably a human patient who is suffering from a medical disorder, and in particular a disorder caused by a viral and/or a bacterial infection, in particular a condition or disorder caused by a retrovirus.

The invention provides pharmaceutical or therapeutic agents as compositions and methods for prophylactic treating a subject, preferably a mammalian subject, and most preferably a human patient who is at risk of (or susceptible to) of a medical disorder caused by a viral and/or a bacterial infection, in particular a condition or disorder caused by a retrovirus. In particular, the invention provides agents, compositions, methods and uses thereof useful to substantially reduce transmission of diseases caused by a viral and/or a bacterial infection, e.g., HIV or other retroviral infections. Subjects at risk for infection, can be identified by, for example, any known risk factors for infection by, for example, HIV.

The invention provides pharmaceutical or therapeutic agents as compositions and methods for prophylactic treating a subject, preferably a mammalian subject, and most preferably a human patient who is at risk of (or susceptible to) of a medical disorder caused by a viral and/or a bacterial infection.

Pharmaceutical compositions of the invention can contain a mixture of polyphenol-quinonoid polymer derivatives according to the invention in any form described herein.

Mixtures of polyphenol-quinonoid polymer derivatives of the invention, together with a conventionally employed adjuvant, carrier, diluent or excipient may be placed separately into the form of pharmaceutical compositions and unit dosages thereof, and such form may be employed as solids, such as tablets or filled capsules, or liquids such as solutions, suspensions, emulsions, elixirs, or capsules filled with the same, all for oral use, or in the form of sterile injectable solutions for parenteral use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. The present compositions may also be in the form of a time-release composition.

Polyphenol-quinonoid polymer derivatives of the invention may be formulated as liquid preparations suitable for oral administration (e.g., suspensions, syrups, elixirs, mouthwash or gargle and the like) which can be prepared according to techniques known in the art and can employ any of the usual media such as water, glycols, oils, alcohols and the like. Polyphenol-quinonoid polymer derivatives of the invention may be formulated as solid preparations suitable for oral administration (e.g., powders, pills, capsules and tablets) which can be prepared according to techniques known in the art and can employ such solid excipients as starches, sugars, kaolin, lubricants, binders, disintegrating agents and the like. Polyphenol-quinonoid polymer derivatives of this invention may be formulated as parenteral compositions which can be obtained through techniques known in the art and typically employ sterile water as a carrier and optionally other ingredients, such as a solubility aid. Polyphenol-quinonoid polymer derivatives of the invention in the form of injectable solutions can be prepared according to methods known in the art wherein the carrier comprises a saline solution, a glucose solution or a solution containing a mixture of saline and glucose.

Formulations for rectal administration may be presented in the form of suppository with a suitable base comprising, for example, cocoa butter. Formulations suitable for vaginal administration may be presented in the form of tablets, vaginal suppository tampons, creams, gels, pastes, foams or spray formulations.

Polyphenol-quinonoid polymer derivatives of the invention may be formulated as topical compositions such as in a form of a cream, a foam or a gel.

Mixtures of polyphenol-quinonoid polymer derivatives of the invention may be used as a mutifunctional antimicrobial agent such as fluorescent antimicrobial stains for prevention of bacterial infection on surfaces and in particular tissues, notably those used in healthcare. In particular, mixtures of polyphenol-quinonoid polymer derivatives of the invention may be incorporated into textiles or paint matrices. As described by Sun, 2005, *J. Chem. Educ.*, 82, 60-64, wherein the compounds may be covalently linked to textiles or covalently linked to other dyes.

Mixtures of polyphenol-quinonoid polymer derivatives of the invention may be used for staining tissue sample in view of their analysis without affecting cell viability.

Further description of methods suitable for use in preparing pharmaceutical compositions for use in the present invention and of ingredients suitable for use in said compositions is provided in *Part* 5 of *Remington's Pharmaceutical Sciences*, 21st Edition, 2005, *University of the Sciences in Philadelphia, Lippincott Williams & Wilkins*, which is incorporated herein by reference.

Mode of Administration

Mixtures of polyphenol-quinonoid polymer derivatives of the invention and compositions thereof may be administered in any manner, including, but not limited to, orally, parenterally, sublingually, topically, in particular topically to epithelia, transdermally, rectally, transmucosally, vaginally, via inhalation, via buccal or intranasal administration, or combinations thereof.

In a particular embodiment, mixtures of polyphenol-quinonoid polymer derivatives of the invention and compositions thereof are administered orally.

In a particular embodiment, mixtures of polyphenol-quinonoid polymer derivatives of the invention and compositions thereof are administered topically.

Mixtures of polyphenol-quinonoid polymer derivatives of the invention and compositions thereof may be administered, at periods of pre-exposure and/or post-exposure to the disease-causing virus and/or bacteria, alone or in combination with effective amounts of one or more further therapeutic agents.

Administration of mixtures of polyphenol-quinonoid polymer derivatives of the invention and compositions thereof for a prophylactic purpose, notably as a as a topically applied prophylactic, can occur prior to the manifestation of symptoms characteristic of an infection, such that the infectious disease or disorder is prevented or, alternatively, delayed in its progression.

According to an aspect of the invention, formulations according to the invention may be associated with or integrated within an article, such as an intrauterine device, vaginal diaphragm, vaginal sponge, condom, etc., notably where time-release and/or mechanical-release of the compositions is achieved, when the article is placed on an appropriate body part or in an appropriate body cavity.

According to another aspect, the uses and methods according to the invention for preventing Gram-positive and Gram-negative bacteria related infections or disorders, comprise a step of coating the apparatus and materials used in healthcare and notably intensive care and surgery (such as textile, surgical material, tubings, ventilators etc. . . . ) by a composition comprising a mixture of polyphenol-quinonoid polymer derivatives according to the invention. Typically, the composition comprising a mixture of polyphenol-quinonoid polymer derivatives according to the invention is incorporated into the surface or sprayed onto the surface of the said apparatus and materials used in healthcare, in particular intensive care and surgery.

Combination

According to one embodiment of the invention, mixtures of polyphenol-quinonoid polymer derivatives according to the invention and pharmaceutical formulations thereof can be administered alone or in combination with a co-agent useful in anti-HIV-1 therapy or an immune system modulator or an antiinfective or antiviral compound, such as a nucleoside reverse transcriptase inhibitor, a non-nucleoside reverse transcriptase inhibitor or HIV protease inhibitor.

According to another embodiment of the invention, mixtures of polyphenol-quinonoid polymer derivatives according to the invention and pharmaceutical formulations thereof can be administered alone or in combination with an antibacterial co-agent or a co-agent useful in the prevention and/or treatment of Gram-positive and/or Gram-negative bacteria related infections or disorders or in the treatment of immunodepressed patients.

Patients

In an embodiment, patients according to the invention are patients suffering from a disease or disorder caused by a viral and/or a bacterial infection, in particular a condition or disorder caused by a retrovirus.

In a further embodiment, patients according to the invention are patients suffering from a disease or disorder caused by HIV, typically HIV-1.

In another further embodiment, patients according to the invention are patients suffering from a disease or disorder caused by HIV variants that are non-nucleoside drug-resistant.

In another further embodiment, patients according to the invention are patients suffering from a disease or disorder caused by HIV variants that are nucleoside drug-resistant.

In another further embodiment, patients according to the invention are patients suffering from a disease or disorder caused by a bacterial infection.

Use According to the Invention

In another embodiment, the invention provides a use of a mixture of polyphenol-quinonoid polymer derivatives according to the invention or a pharmaceutical composition thereof for the preparation of a pharmaceutical preparation for the prevention and/or treatment of a disease or disorder caused by a viral and/or a bacterial infection, in particular a condition or disorder caused by a retrovirus.

In another embodiment, the invention provides a method of preventing and/or treating or repressing a disease or disorder including, said method comprising administering in a subject in need thereof a therapeutically effective amount of a mixture of polyphenol-quinonoid polymer derivatives according the invention or a formulation thereof.

According to a further embodiment, the invention provides a method of preventing and/or treating or repressing a disease or disorder according to the invention wherein the disease or disorder is a viral condition caused by a retrovirus.

According to a further embodiment, the invention provides a use or a method according to the invention wherein the mixture of polyphenol-quinonoid polymer derivatives according the invention or a formulation thereof is to be administered orally.

According to another further embodiment, the invention provides a use or a method according to the invention wherein the mixture of polyphenol-quinonoid polymer derivatives according the invention or a formulation thereof is to be administered topically.

According to a further embodiment, the invention provides a use or a method according to the invention wherein the disease or disorder is caused by HIV-1.

According to another further embodiment, the invention provides a use of a mixture of polyphenol-quinonoid polymer derivatives according to the invention as a multifunctional antibacterial agent or for the preparation of a multifunctional antibacterial composition as they have dye and pigment characteristics (shades of brown and yellow, as well as, being self-fluorescent thereby acting as fluorescent stains) such as described in Ma et al., 2003, 58(1), pp. 27-3.5; Gao, 2008, *Textile Research Journal*, 78(1), 60-72 and Wainwright et al., 2003, *Biomedicine, Biotechnic & Histochemistry*, 78(3-4): 147-155.

According to another further embodiment, the invention provides a use of a mixture of polyphenol-quinonoid polymer derivative according to the invention as a bacterial staining agent or for the preparation of a bacterial staining composition for example for use in microscopic imaging of contaminated cell and tissue samples.

Synthesis of Compounds of the Invention:

The invention further provides a new process of preparation of polyphenol-quinonoid polymer derivatives, in particular mixtures of polyphenol-quinonoid polymer derivatives according to the invention. In a particular embodiment, the invention provides a process of synthesizing polyphenol-quinonoid polymer derivatives comprising the following steps:

a) slowly adding sequentially, under stirring and in the dark, recrystallized hydroquinone, 1,4 benzoquinone and phenol to nanopure triple distilled water which pH has been previously adjusted to about 12 (after addition of all the reactants), in a molar ratio of 2.73; 0.93; 0.13 (of hydroquinone to benzoquinone to phenol);

b) leaving the mixture obtained under step a) in the dark at room temperature under continuous stirring for about 24 hours;

c) adjusting the pH of the solution to about 1.5, typically by the addition of HCl;

d) filtering the product precipitate and rinsing with ice-cold water followed by drying the solid obtained under step c).

The fraction isolated under step d) is a mixture of polymers according to the invention comprising the higher molecular weight polymer fractions (e.g. >266 g/mole and <1,000 g/mole).

The invention further provides a new process of preparation of polyphenol-quinonoid polymer derivatives, wherein the process of the invention further comprises a step e) of collecting the filtrate from the above filtration, drying, dissolving in absolute ethanol (concentrate and then cool the solution in order to precipitate out inorganic salts), filtering out the salts and drying the remaining solids. The fraction isolated under step e) is a mixture of polymers according to the invention comprising the lower molecular weight polymer fractions (approximately 266 grams/mole and lower).

Alternatively, it has been found that phenol might be removed and NaOH might be added under step a), wherein the molar ratio of NaOH to hydroquinone and to 1,4 benzoquinone is about 3:1:1. In this case, the reaction can either be conducted in water or in alcohol medium such as in propanol, methanol or ethanol or a mixture thereof. Kinetics of reaction step a) when conducted in alcohol medium is increased and therefore the reaction step decreased advantageously down to about from 2 hours to about 10 minutes. In this case, it has been also found that step a) may be conducted in the dark or under near UV radiations in order to accelerate the formation of larger molecular weight polymer fractions. Stabilization of the reaction under prolonged UV radiation (e.g. such as >24 h) might be achieved by the addition of small amounts of phenol (e.g. 1% or less) to the reactants under step a) in order to avoid ring opening reactions. Such a process allows achieving an easier and quicker synthesis, in particular for smaller molecular weight fractions with increased yield (typically yields for smaller molecular weight fractions are increased by approximately 55% as compared to the process described above) and the quantities of needed phenol are reduced. This method also allows to collect the higher molecular weight fractions of the polymer mixture of the invention (e.g. typically molecular weight polymers higher than about 266 g/mole and lower than 1,000 g/mole) after the reaction is being stopped after about 10 minutes by adjusting the pH to about 1.0 and the solid are filtered out. This method further allows a highly simplified purification step of lower molecular weight fraction of the polymer mixture of the invention (e.g. lower than about 266 grams/mole) as purification of the solids from the obtained filtrate can be simply carried out by dissolving them in absolute ethanol in order to precipitate out and filter out inorganic salts, as described by Pinho et al., 2005, *J. Chem. Eng. Data,* 50, 29-32. Once the salts are filtered out, the alcohol is evaporated and the purified solid comprising the mixture of the polymers according to the invention, collected.

In another particular embodiment, a process of synthesizing a mixture of polyphenol-quinonoid polymer derivatives comprising the following steps:

a) slowly adding sequentially, under stirring and in the dark, NaOH pellets to recrystallized hydroquinone and 1,4 benzoquinone to nanopure triple distilled water or to an alcohol (e.g. in propanol, methanol or ethanol or a mixture thereof), in a molar ratio NaOH to hydroquinone to benzoquinone of 3:1:1;

b) leaving the mixture obtained under step a) in the dark at room temperature or under near UV radiation under continuous stirring for about 24 hours;

c) Adjusting the pH of the solution to about 1.0, typically by the addition of HCl and turning off the UV radiation source when carried out under UV radiation and leaving the solution for at least 4 hours at room temperature;

d) collecting the solids formed under step c) comprising the higher molecular weight fractions of the polymer, typically by filtration and rinsing with ice cold water and collecting and drying the filtrate comprising the lower molecular weight fractions of the polymer. The lower molecular weight fractions are purified by first drying the filtrate, then dissolving in absolute ethanol, cooling the solution and filtering out inorganic salts which precipitate. Finally the ethanol is evaporated and the lower molecular weight polymers are collected.

In a further particular embodiment, very small stoichiometric amounts of phenol (e.g. about 1%) can be added to the reactants under step a) to stabilize the reaction, especially when step b) is to be carried out under UV radiation and/or for very long periods of time (>24 hours). Longer periods of time allowed for the reaction synthesis result in relatively larger amounts of larger molecular weight fractions (>300 g/mol and <1000 g/mol).

In another particular embodiment, the raw products obtained under step d) might be stored (for example for further purification or simple storage), the storage being carried out such as the product remains in the darkness while storage, typically in dark or amber coloured vessels, preferably in a dark cool location, most preferred in a cool, dry, dark location.

In a further aspect, the invention provides a process of synthesizing polyphenol-quinonoid polymer derivatives comprising a step of purifying the products obtainable under step d), e.g. removing inorganic salts and side products. Typically, the said purification step comprises the following steps:

e) dissolving the product obtainable under step d) in a solvent such as ethanol;

f) eluting the mixture on a purification column;

g) evaporating the solvent from the eluted product;

h) eliminating water from the solid obtained from step g).

Typically, step f) may be performed on a silica gel column prepared with 70% 2-propanol as the mobile phase. Evaporation under step g) may be carried out by fanning off the solvent with air. Elimination of water under step h) may be carried out by a series of successive evaporations followed by vacuum filtrations followed by prolonged drying (e.g. by drawing air through the solid by continuing the suction process, typically for about 60 minutes). The product may be further pulverized and then placed in a desiccator jar in the presence of a desiccant such as drierite to desiccate the product mixture. In a particular embodiment, the purified product obtained under step h) might be stored for further filtration, the storage being carried out such as the product remains in a dark, cool and dry environment, while storage, typically in dark or amber coloured vessels.

In a further aspect, the invention provides a process of synthesizing polyphenol-quinonoid polymer derivatives comprising a step of filtrating a purified product obtainable under step h). Typically, the said filtration step comprises the following steps:

i) dissolving the product obtained under step h) in nanopure water; and f) ultra-filtrating the re-dissolved solid to retain molecular weights lower or equal to 1000 g/mol.

The product may be then further dried and stored in such conditions that the product remains in a dark, cool and dry environment, while storage, typically in dark or amber coloured vessels.

The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

General Procedures & Conditions

The following studies are conducted to support the high antiviral activity of polyphenol-quinonoid polymer derivative according to the invention and their low toxicity.

The following abbreviations refer respectively to the definitions below:

ppm (parts per million), CCR5 (chemokine coreceptor 5), DDI (didanosine), EPR (Electron paramagnetic resonance), FITC (Fluorescein isothiocyanate), FIV (feline immunodeficiency virus), GFP (green fluorescent protein), HIV (Human Immunodeficiency Virus), MFI (mean fluorescence intensity), NMR (nuclear magnetic resonance), PBS (phosphate buffer sulfate), RT (reverse transcriptase), SD (standard deviation), UV (ultraviolet).

Example 1

Synthesis and Characterization of Polyphenol-Quinonoid Polymer Derivatives According to the Invention Polyphenol-quinonoid polymer derivatives according to the invention are formed through a novel autocatalytic free radical reaction according to the invention and as described below.

Reagent preparation, weighing of starting materials and the synthesis reaction must be carried out in the dark at room temperature without the use of additional oxidation agents (open air oxidation is sufficient). Starting materials are to be kept separate until ready for use. Deviation in any one of these experimental parameters will lead to uncontrolled complex free-radical degradation, condensation, ring opening and fragmentation reactions.

The pH of the nanopure water is first adjusted to pH 12 by addition of NaOH pellets, while stirring. It is important that no oxidation, reducing or buffering agents or compounds be added at this or any other point in the procedure. Recrystallized hydroquinone 1,4 benzoquinone and phenol are then slowly added to nanopure water, in the dark, with stirring. The order of addition to solution is important.

The precise molar ratio of reactants used for the preparation of the present polyphenol-quinonoid polymer mixture ("polymer-1 mixture") is 2.73:0.93:0.53 of hydroquinone to benzoquinone to phenol. The molar ratios are important in that different molar ratios will lead to different ratios of components in the final polymer reaction product.

The solution is left in the dark at room temperature with continuous stirring for 24 hours. Although all of the starting materials are used up within the first few hours of reaction, polymerization reactions continue and are complete within about 24 hours. When the reaction is complete, the pH is adjusted to 6.5 by a drop wise addition of concentrated HCl. The solution is then dried and the remaining solid stored in amber colored sample bottles.

Purification (removal of inorganic salts and side products), was performed by taking 35 g of the product obtained as described above at a time and dissolving in 100 mL of absolute ethanol. This mixture was placed on a silica gel column (5.0 cm{D}×100 cm, prepared with 70% 2-propanol as the mobile phase. Once the ethanol mixture was eluted on to the column, the product mixture was eluted off the column with 70% 2-propanol. The solvent was evaporated from the elution mixture by fanning off the solvent with air. Since the product mixture retained a great deal of water, the solid products were recovered by a series of successive evaporations followed by vacuum filtrations followed by prolonged drying by drawing air through the solid by continuing the suction process for 60 minutes. The so-obtained product was pulverized and then placed in a dessicator jar in the presence of drierite to desiccate the product mixture. The final product is then stored in amber bottles in a cool/dry/dark location.

When ready for use in antimicrobial studies, the material is simply redissolved as needed in nanopure water and the resulting solution is ultrafiltrated with a molecular weight cut-off membrane. The polymers with molecular weights under 1000 g/mol are retained dried and stored until needed in amber colored bottles. These are the polymers referred to as "Polymer 1" in this study. For analyses of viral replication and cytotoxicity, the polyphenol-quinonoid polymer according to the invention was suspended in culture media.

Different polyphenol-quinonoid polymer products can be formed, with similar antiviral and antimicrobial properties by controlling the concentrations of the various components of those polyphenol-quinonoid polymer derivatives by simply varying the molar ratio of any one of the 3 initial reactants. The different polymer mixtures will have varying chemical, physical, spectroscopic and anti-microbial properties. For the sake of comparison, a synthetic hydroquinone humate-derived analogue ("polymer 2"), whose structure is similar to HS-1500 as described in Schneider et al., 1996 (or EP 0537 430 B1), is used as control (molecular weights up to and greater than 1,500 grams per mole, were retained (HS-1500), consisting of aliphatically linked aromatic rings with carboxylic functional groups, obtained after strong chemical oxidation of hydroquinone at pH 10).

Chemical Characterization

Product characterization and confirmation is performed using standard spectroscopic techniques for similar compounds, as described earlier (Patai, 1989, *Chemistry of the Quinonoid Compounds* (Wiley, New York), Ariese et al., 2004, *Aquatic Sciences,* 66(1), 86-94; Bruccoleri et al., 2000, above). The procedures and protocols for these analytical techniques on similar compounds, are well known to the skilled person and have been documented in the literature in detail (Patai, 1989, above). Standard techniques such as Carbon-13 nuclear magnetic resonance ($^{13}C$ NMR), mass spectrometry and elemental analysis were used. UV-visible spectroscopy, fluorescence and EPR were also used.

$^{13}$C-NMR spectra of the polyphenol-quinonoid compound according to the invention and obtained above ("polymer 1"), showed two relatively narrow bands centered near 149 ppm and 117 ppm (FIG. 1A). The first band near 149 ppm has been assigned to aromatic carbons bonded to oxygen (two types of aromatic carbon oxygen bonds occurring in these molecules: 1) hydroxyl (OH) substitution at aromatic carbon centers and 2) oxygen bridges linking aromatic rings together), while the second band near 117 ppm has been assigned to aromatic carbons at unsubstituted carbon centers. Significant peaks from mass spectrometry occurred at 542 and 434 g/mol. These findings were entirely consistent with reported $^{13}$C-NMR assignments in the literature for similar molecules and computational chemistry calculations (Patai, 1989, above; Ralph, 2004, *L. L. a. R. J., US Forest products Laboratory, US Dairy Forage Research Center and USDA Agriculture Service*, pp. 1-18). Elemental analysis of a fraction (250 g/mole) of the polymer mixture resulted in approximately 58% C atoms; 4% H atoms and the remainder oxygen atoms. Ultraviolet-visible spectrum showed broad featureless absorbance between 200-400 nm, a characteristic representative of charge-transfer, donor-acceptor complexes formed of similar molecular polymers (Ariese et al., 2004, *Aquatic Science*, 66, 86-94; Bruccoleri et al., 1993, *Environmental Science & technology*, 27, 889-894; Bruccoleri et al., 2001, *Molecular modeling of humic structures* in E. A. Ghabbour and G. Davies (Eds.), *Humic substances: Structures, models, and functions*, London: The Royal Society of Chemistry, 193-208).

Polymers were found to be stable even after 12 months in powder form stored in dark amber colored bottles in a cool dry location (as their chemical characterization was unchanged).

As confirmed by the above characterizations, the polyphenol-quinonoid compound according to the invention obtained above is composed of a mixture of oxygen bridged aromatic rings, having few hydroxy substitutions have a general formula (I), wherein n=1−x; where x=2-10, where the molecular weight fraction <1,000 g/mol was isolated (n=1-2 retained).

Measurement of Polymer Fluorescence

Astrocytes (U373 cells) were cultured as earlier described (Zhang et al., 2003, *J. Virol.*, 77, 6899-912; Boven et al., 2003, *J. Immunol.*, 170, 2638-46) and treated with polyphenol-quinonoid compound according to the invention obtained above at concentrations ranging from 0.01 mM to 1 mM. Following incubation for 24 h at 37° C., cells were examined for fluorescence using an inverted Fluorescent Microscope (Zeiss) at 400 nm wavelength. The experiment showed that there was a concentration-dependent accumulation of fluorescence in the cytoplasm of treated cells compared to untreated cells. At 1,000 µM a bright fluorescence was observed without showing any adverse effects on cell viability Polymer Cytotoxicity HeLa-CD4/CCR5 cells were plated in 96 well plates of 50,000 cells/well, as earlier described (Jones et al., 2005, *Virology*, 334, 178-193) and the polyphenol-quinonoid compound according to the invention obtained above was applied to cultured cells in a concentration-dependent manner. Following 6 and 24 hours of exposure to the compound, cell death was assessed by trypan blue dye exclusion. Experiments revealed that maximal cytotoxicity reached approximately 5% in HeLa-CD4/CCR5 at 10 µM, while the 50% cytotoxicity (TC$_{50}$) of HS-1500, a synthetic hydroquinone humate-derived analogue whose structure is similar to polymer 2, was about 600 µg/ml (Schneider et al., 1996, above) (FIG. 7).

Polymer Dosing and In Vivo Toxicity Studies

To determine the safety of the polymers, mice were treated with "polymer 1" in a dose-dependent fashion (2, 20, 200 mg/Kg per os daily) for one week and thereafter, animals were euthanized and assessed by histological methods for evidence of cell injury including evaluation of gut, spleen, liver and heart. Histological analysis of liver, gut and spleen from animals treated with the polymer did not reveal deviations from that of control groups. Histological analysis of sections from gut, liver and spleen from mice treated orally with "polymer 1" (200 mg/kg) showed no evidence of toxicity nor were there any apparent morbidity or mortality associated with treatment of animals following one week of treatment.

These in vitro and in vivo results suggest the safety profile of "polymer 1", notably as compared to didanosine, a known antiretroviral nucleoside reverse transcriptase inhibitor, that induces decreased viability of HeLa-CD4/CCR5 at high concentrations (1,000 µM).

Alternative Synthesis and Characterization

An alternative synthetic procedure was used and proved to lead to the same polymer mixture. The polymer mixture was synthesized according to an alternative process according to the invention where NaOH was added to recrystallized hydroquinone and 1,4 benzoquinone to nanopure water or to alcohol in stoichiometric amounts where the molar ratio of NaOH to hydroquinone to benzoquinone was of 3:1:1. The solution is left in the dark at room temperature with continuous stirring for 24 hours. Although all of the starting materials are used up within the first few minutes of reaction, polymerization reactions continue and result in larger polymer fractions if left for a longer period of time and/or under more concentrated conditions and/or by using near ultraviolet light. The reaction is stopped by adjusting the pH to 1.0 by the drop wise addition of concentrated HCl. The polymers are then collected as described above. When ready for use in antimicrobial studies, the material is simply redissolved as needed in nanopure water. The larger more insoluble fractions need to be adjusted to a biologically significant pH (e.g. pH 7.4), in order to dissolve more efficiently. The resulting solution is then ready for use. Alternatively, the compounds may be given orally without first adjusting the pH in water. Ultraviolet spectra, elemental analysis and mass spectrometry results were consistent with the expected molecular structures described above. For example, peaks from mass spectrometry representing expected molecular weight fractions at 542, 390 and 266 g/mol were found.

Example 2

In Silico Modelization

Molecular modeling prediction of these compounds interacting at an HIV-1 RT active site is conducted. Molecular modeling studies show that the polyphenol-quinonoid polymers according to the invention may bind to several critical components of the HIV-1 RT enzyme. Semi-empirical geometrical optimization PM3 level calculation for a representative structure of a polyphenol-quinonoid polymer according to the invention having molecular weight of 434 g/mol (n=2) allows to show an electrostatic potential mapping on the electron density surface with high electron density ('hot') and low electron density regions ('cold'). These alternate regions of hot and cold electron density are typical for selfassociating, self-assembling molecules and allow for complementary interactions to occur ('hot' regions with 'cold' regions to form dimers for example). After 0.5 hr of iterations under a Sybyl force field, the modeling results show binding interaction conformational changes at the HIV-1 RT RNase H active site near amino acid residue Tyr441. The metal ion cofactor $Mg^{2+}$ atom appears just above Tyr441. Molecular modeling revealed strong binding interaction at the RNase H active site via two major interactions in coordination with the metal ion cofactor ($Mg^{2+}$) and aromatic π-π stacking interactions with the important conserved aromatic amino acid residue Tyr501. Other binding interactions were predicted to be near the Trp229, Met230, Gly231 and Tyr232 quartet, which is important for the DNA polymerase and RNase H domains. Further, binding interactions also occurred near Trp266 in the minor groove binding track. There also appears to be some $Mg^{2+}$ coordination displacement near the catalytically essential acidic residue Asp443 and aromatic residues Tyr457 and Tyr441 in the RNase H active site. Such displacement of critical metal ions and conformational changes in the HIV-1 RT enzyme predict the inhibitory capacity of a polyphenol-quinonoid polymer according to the invention towards the enzyme and therefore the virus.

Modeling further reveals a structure for polyphenol-quinonoid polymers according to the invention which is relatively flat and very flexible (single bond oxygen bridged aromatic rings) and can form self-assembly structures. Their high degree of conformational freedom (even when bound at an active site) makes them excellent candidates as HIV-1 RT inhibitors as their degrees of conformational freedom at an active site (molecular 'wiggling'), albeit restricted and localized at the active site, will help overcome mutational resistance of the virus by allowing the binding polymers to adjust and adapt to slight conformational changes in mutated forms of the active site.

Further semi-empirical geometrical optimization PM3 level calculation for a representative structure of a polyphenol-quinonoid polymer according to the invention having molecular weight of 266 g/mol (n=1) gave lead to similar conclusions which are entirely consistent with the possibility of forming charge transfer-like dimers which may have relatively high conformational freedom and cause low temperature fluorescence line broadening even at very cold temperatures (10 K), as described by Ariese, et al., 2004, *Aquatic Science*, 66, 86-94.

Example 3

Effect of Polyphenol-Quinonoid Polymer Derivatives According to the Invention on Reverse Transcriptase Activity In order to assess the anti-viral activity of a polyphenol-quinonoid mixture according to the invention, the following assay was carried out to study its effect on RT activity.

For assessment of viral infection, Peripheral Blood Mononuclear Cells (PBMCs) from healthy humans (as described in Jones et al., 2005, above) and cats were initially stimulated with Con-A and subsequently infected after 3 days with the lentivirus together with introduction of IL-2 in tissue culture supernatants, which were harvested at different intervals as described earlier (Zhang et al., 2003, above).

Reverse transcriptase activity in culture supernatants was measured as described previously (Johnston et al., 2000, *J. Virol.*, 74, 7211-20). Briefly, 10 µl of supernatant was cleared of cellular debris by centrifugation and incubated with 40 µl of reaction cocktail containing [$^{32}$P]dTTP for 2 hours at 37° C. Samples were blotted on DE81 ion-exchange chromatography paper (Whatman International, Maidstone, UK) and washed 3 times for 5 minutes in 2×SSC and twice for 5 minutes in 95% ethanol. Reverse transcriptase levels were measured by liquid scintillation counting. All assays were performed in triplicate and repeated a minimum of 2 times.

Alternatively, similar experiments were conducted on a cellular growth assay in MT-2 cells infected with HIV wild-type and HIV drug-resistant variants (nucleoside drug resistant virus (K65R) strains and non-nucleoside resistant strains associated with drug resistance: K103N and D30N (Winters et al., 2000, *Antiviral Therapy* 5: 57-63), via measurement of $IC_{50}$ in a growth assay in MT-2 cells (RT activity assay) as described in Wainberg et al., 2010, *Antimicrob. Agents Chemother*, doi:10.1128/AAC.01795-09. $IC_{50}$ values for lower molecular weight (MW) fractions (more water-soluble fraction) and higher molecular weight fractions of the mixture of the invention are indicated in Table 1 below.

TABLE 1

| | IC50 (mg/ml) | | | |
| --- | --- | --- | --- | --- |
| Composition (MW fraction) | Wild-type virus | Nucleoside-resistant virus (K65R) | Non-nucleoside-resistant virus (K103N) | Non-nucleoside-resistant virus (D30N) |
| <266 g/mole | 2.4 | 2.0 | 1.9 | 2.4 |
| 266 < MW < 1'000 g/mole | 3.8 | 5 | 5.3 | 5.7 |

Those results show that a mixture according to the invention is able to inhibit HIV replication not only of wild-type virus but also against HIV variants that are non-nucleoside drug-resistant.

FIV replication was also assessed by reverse transcriptase activity in PBMCs and in feline lymphocyte cell line (MYA-1) supernatant.

Figure 2:
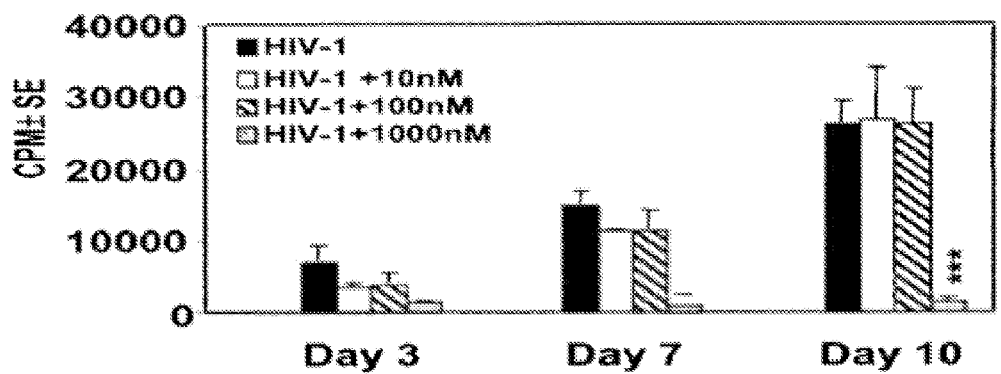
FIG. 2: Inhibitory activity of viral reverse transcriptase levels and activity of a polyphenol-quinonoid polymer according to the invention measured as described in Example 3 A & C: RT levels in the supernatant of viral inoculum in human PBMCs infected by HIV-SF162 treated with various concentrations of a polyphenol-quinonoid polymer according to the invention versus control (no treatment); B & D: RT levels in the supernatant of viral inoculum in MYA-1 cells infected by FIV-Ch treated with various concentrations of a polyphenol-quinonoid polymer according to the invention versus control (no treatment); E & F: RT levels in the supernatant of viral inoculum in human PBMCs infected by HIV-SF162 (E) or in the supernatant of viral inoculum in MYA-1 cells infected by FIV-Ch (F) and treated with various concentrations of control "polymer 2".
Figure 2:
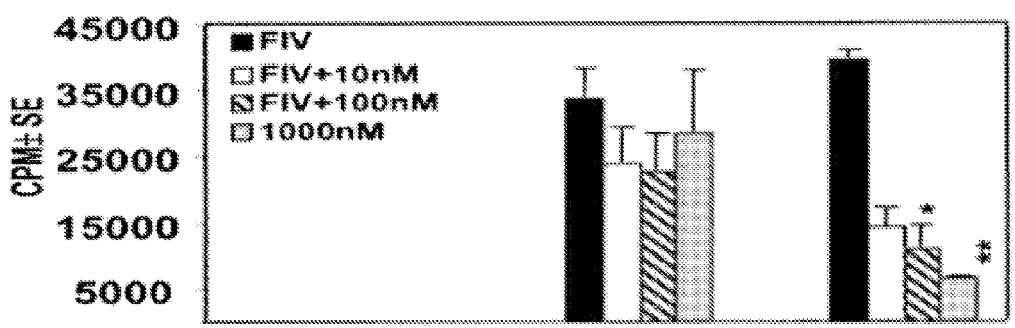
Figure 2:
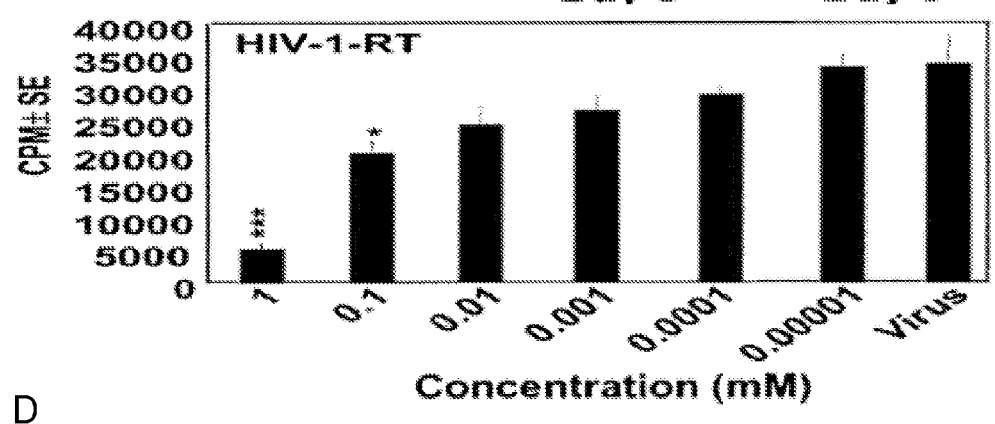
Figure 2:
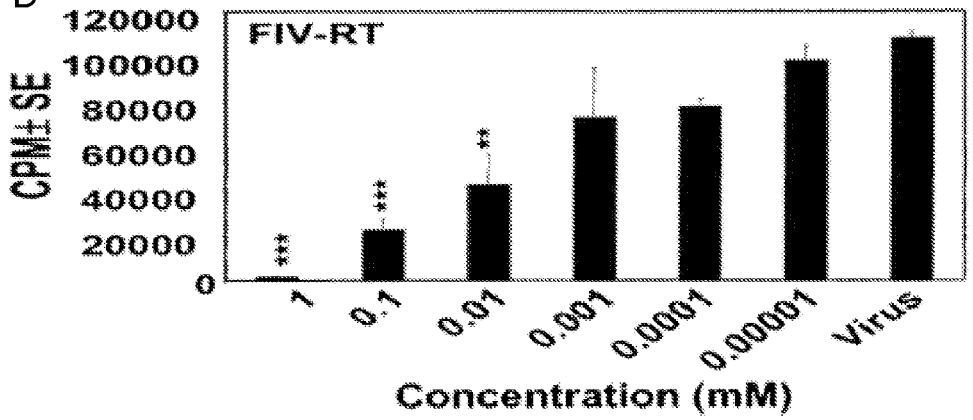
Figure 2:
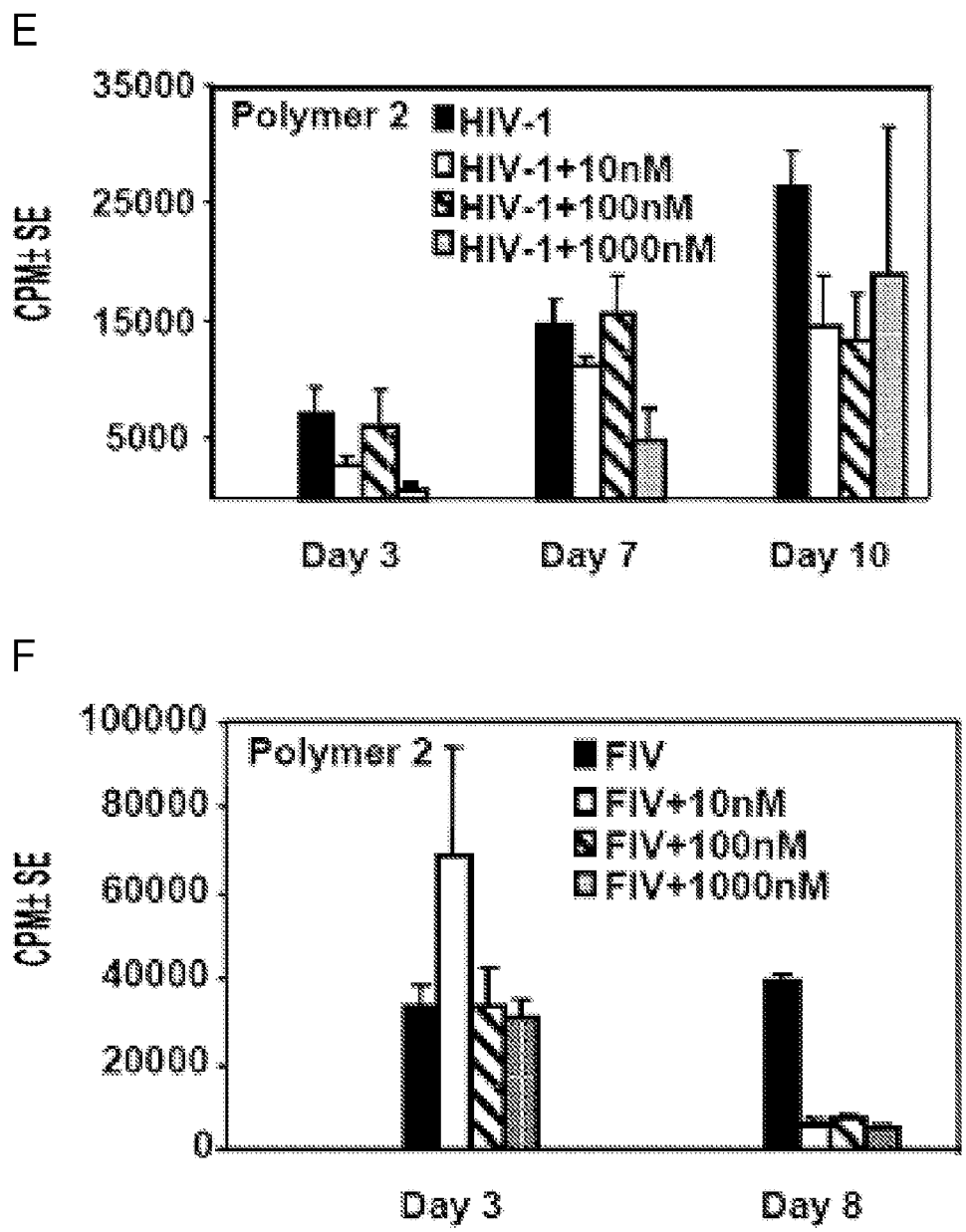

Analysis of RT levels in human PBMCs infected by HIV-1 (FIGS. 2A and 2C) and MYA-1 cells infected by FIV (FIGS. 2B and 2D) revealed a concentration-dependent inhibition of RT activity by "polymer 1" in HIV-1-infected PBMCs (FIG. 2C) that was most effective at Day 10 (FIG. 2A) (P<0.001) and FIV-infected MYA-1 cells (FIG. 2D), effective at Day 8 (FIG. 2B) (P<0.01), compared to control "polymer 2", which was not effective in this assay (FIGS. 2E & F). The $IC_{50}$ values for polymer 1 against two different FIV strains were 126 nM (FIV-Pet) and 151 nM (FIV-Ch) while for control "polymer 2", the $IC_{50}$ values were 1096 nM (FIV-Pet) and 50 nM (FIV-Ch). Though maximal cytotoxicity was achieved at 10 µM, the $IC_{50}$ of polymer 1 for inhibition of viral replication in vitro was 40 nM (against HIV-1) and 10 nM (against FIV), while for control "polymer 2", the $IC_{50}$ values were 245 nM (against HIV-1) and 9 nM (against FIV).

Supernatants from infected cells revealed a substantial reduction of RT activity in a polymer concentration-dependent manner. There was a significant reduction in HIV-1 RT activity in supernatants treated with 1,000 µM and 100 µM of "polymer 1" (FIG. 2C) and in FIV RT activity in supernatants treated with 1,000 µM, 100 µM and 10 µM of "polymer 1" (FIG. 2D).

Therefore, polyphenol-quinonoid compounds according to the invention reduce both HIV-1 and FIV reverse transcriptase (RTase) activity in a concentration dependent manner in infected cultures (p<0.05). Further, these results suggest that the mechanism by which the polymers of the invention act might be through direct inhibition of RT.

Example 4

Effect of Polyphenol-Quinonoid Polymer Derivatives According to the Invention on HIV-1 p24 Protein Expression Various assays were performed to determine the effect of a treatment with a polyphenol-quinonoid compound according to the invention on HIV-1 p24 protein expression. Using a flow cytometry approach as described below, p24 levels in HIV-1-infected CEM-GFP cells that were treated with "polymer 1" (20 µM) were examined.

Figure 3:
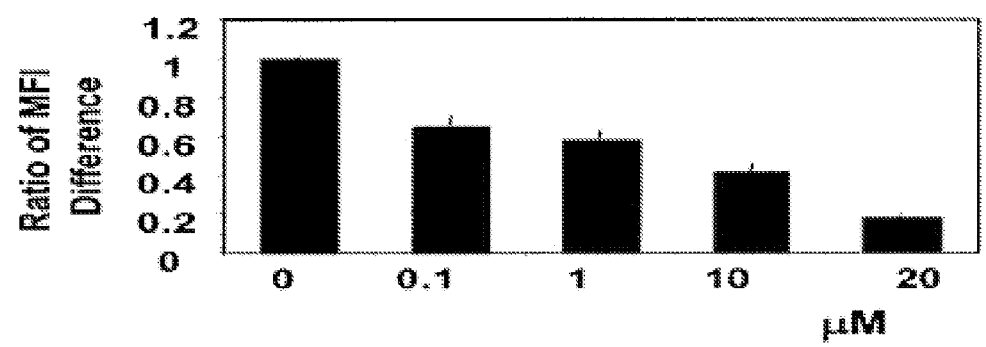
FIG. 3: Effect of a polyphenol-quinonoid polymer according to the invention on viral p24 levels as assessed by flow cytometry fluorescence of labeled p24 antibody (A & B) in cells infected with HIV-NL4-3 strain subsequently treated with "polymer 1" at various doses, as described in Example 4 and as assayed by p24 immunoreactivity (C) as described in Example 4. A: FACS plot for CEM-GFP cells infected by HIV-NL4-3 strain; B: FACS plot for HIV-1 infected 8E5 cells. The ratio of mean fluorescence intensity (MFI) difference is normalised to the isotype antibody control; C: p24 positivity in HeLa-CD4/CCR5 cells infected with two different HIV-1 strains (NL4-3 and SF-162) for various doses of polymer 1 (P-1) as compared to a conventional retroviral drug, didanosine (DDI).
Figure 3:
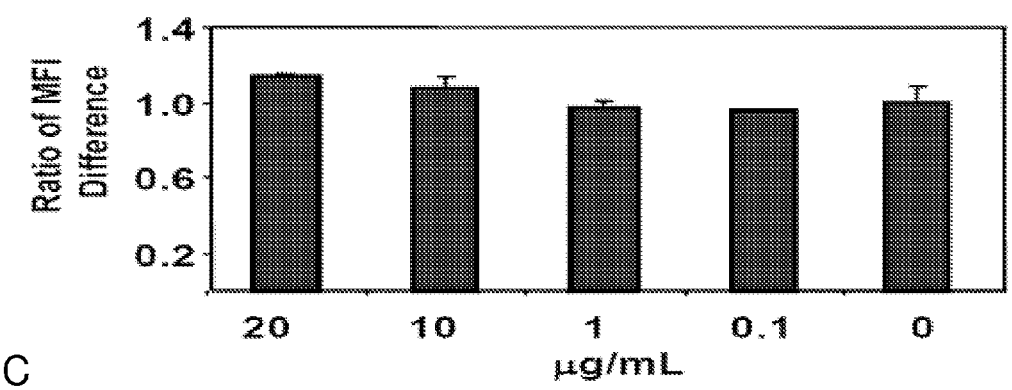
Figure 3:
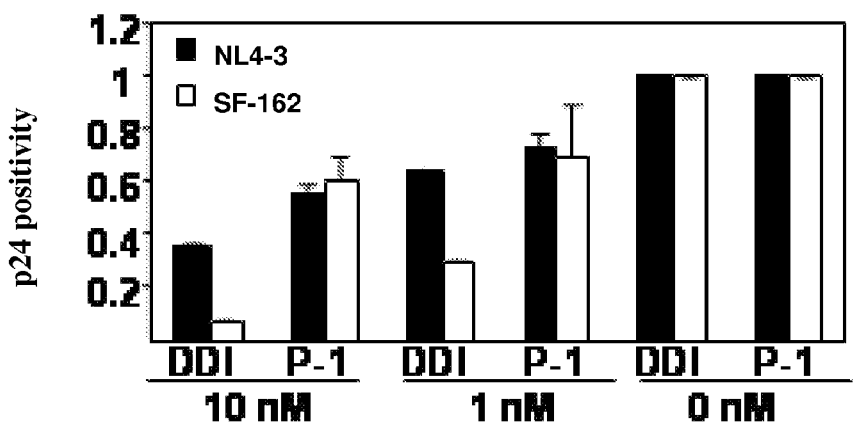

In CEM-GFP cells, an increase in viral infection activates the HIV-1 LTR, which in turn is indicated by higher GFP expression. "Polymer 1" treatment resulted in reduced GFP expression, indicating reduced LTR activation in trans and therefore that the polymer suppresses reverse transcriptase and subsequently p24 expression (FIG. 3A). However, a similar approach with HIV-1-infected 8E5 cells (i.e. cells that produce endogenous HIV-1 proteins) did not reduce p24 levels (FIG. 3B), indicating that the polymer exerts its effect on the virus prior to its transcription, as lower levels of p24 would otherwise indicate suppression of HIV-1 propagation after integration.

To further confirm these findings, p24 immunoreactivity in HeLa-CD4/CCR5 (was determined as described below. A significant decrease in p24 immunopositivity in HeLa-CD4/CCR5 cells infected with two HIV-1 strains (NL4-3 and SF-162) and subsequently treated with "polymer 1" in a dose-dependent fashion was observed (FIG. 3C). The suppression of p24 levels was comparable to that of a conventional anti-retroviral compound, didanosine (DDI).

Syncytia formation in HeLa-CD4/CCR5 cells was quantified as described below. Significant reduction in syncytia formation in HeLa-CD4/CCR5 cells treated with "polymer 1" prior to infection by HIV-1 was observed (FIG. 3C). In addition to these studies, treatment of HeLa-CD4/CCR5 cells with "polymer 1" prior to infection with a HIV-1 pseudotyped virus as described below revealed a similar concentration-dependent inhibition of luciferase activity.

Thus, these results show that "polymer 1" inhibits HIV-RT resulting in reduced levels of p24 antigen in the infected cells supporting the RT data obtained above.

Flow Cytometry Analysis

Cultured PBLs ($1 \times 10^4$) were labeled with anti-feline CD4, and anti-feline CD8 monoclonal antibodies. FITC-conjugated goat anti-rabbit IgG Ab and PE conjugated goat anti-mouse IgG1 antibodies were applied after labeling of primary antibodies. Omitting the primary antibodies served as controls. To examine the effect of "polymer 1" on p24 expression, HIV-1-infected 8E5 cells (Achkar et al., 2000, *J. Acquir. Immune Defic. Syndr.*, 24, 203-10) or CEM-GFP cells that are stably transfected with GFP under IIIV-1 LTR promoter (Gervaix et al., 1997, *Proc. Natl. Acad. Sci. U.S.A*, 94, 4653-8) were used in a flow cytometry assay.

The CD4 deficient T cell line, 8E5, a subclone of LAV infected A3.01 cells (contains a single integrated copy of proviral DNA directing synthesis of defective particles. These cells produce p24 protein, but not reverse transcriptase (NIH AIDS depository). CD4 deficient T cell were cultured and infected with FIV or HIV-1 as described earlier (Zhang et al., 2003, above; Power et al., 1998, *J. Virol.*, 72, 9109-15) and subsequently. 8E5 cells were pre-treated with different doses of "polymer 1", fixed and permeabilized with BD cytofix/cytoperm kit and immunostained with FITC-labelled p24 antibody KC57. CEM-GFP cells ($2 \times 10^6$) were infected with the NL4-3 strain of HIV-1 ($4 \times 10^6$ cpm) and immediately treated with "polymer 1". After 7 days, cells were washed and GFP fluorescence was examined. Analysis was performed using the FACScan (Becton Dickinson, Mountain View, Calif.) flow cytometer as described previously (Power et al., 1998, above).

Syncytia Formation

Syncytia formation in HeLa-CD4/CCR5 cells was quantified following infection with a syncytia-forming virus (NL4-3) as previously reported (Gang et al., 2004, *Virology*, 330, 424-36). HeLa-CD4/CCR5 cells were cultured as described earlier (Zhang et al., 2003, above; Boven et al., 2003, above). Approximately, $2 \times 10^5$ target cells (HeLa-CD4/CCR5) were infected with HIV virus together with treatment with "polymer 1" and "polymer 2" and after 24 h, adherent cells were fixed with 0.5% glutaraldehyde in PBS. Syncytia formation was scored under ×20 magnification by observation on an inverted Zeiss (Oberkochen, Germany) Axioskop 2 light microscope.

Pseudotyped Virus Infection

Plasmids expressing firefly luciferase within an env-inactivated HIV-1 clone (pNL-Luc-E$^-$R$^-$) and an expression vector (pCMV) containing the HIV-1 JRFL env sequence (Jones et al., 2005, above) were co-transfected into 293T cells and the resulting HIV-JRFL-env pseudotyped virus in the supernatants were harvested 2 days post-transfection, cleared of cell debris by low-speed centrifugation, and used to infect HeLa-CD4/CCR5 cells. Infection of target cells by pseudotyped virus led to expression of luciferase, which was quantified in cell lysates 2 days following virus addition with the Luciferase Assay Kit (PharMingen), and infectivity was expressed as relative light units (Zhang et al., 2003, above).

Example 5

Effect of Polyphenol-Quinonoid Polymer Derivatives According to the Invention on FIV-Infected Cats Feline immunodeficiency virus (FIV) causes an AIDS-like syndrome in the domestic cat, with marked similarities to HIV-1-AIDS in terms of viral properties and pathogenic effects. FIV seroconversion in cats typically manifests itself as a transient acute-phase syndrome, characterized by febrile episodes, lymphadenopathy, neutropenia, and weight loss (de Rozieres et al., 2004, *J. Virol.*, 78, 8971-82). This initial phase is followed by a protracted asymptomatic period with progressive loss of CD4$^-$ T lymphocytes and a terminal AIDS phase characterized by succumbing to opportunistic infections. Thus, this model represents an amenable animal model for testing certain anti-HIV-1 drugs in vivo.

Therefore, in order to support anti-HIV activity of the polyphenol-quinonoid polymer derivatives according to the invention, "polymer 1" was assayed in such a model as follow.

Three-month old cats infected with the recombinant FIV strain, FIV-Ch, were maintained as previously reported (Kennedy et al., 2004, *Aids*, 18, 1241-50) in accordance with CCAC guidelines. Oral treatment with "polymer 1" (twice daily by gavage) was initiated in 4 twelve-week old chronically FIV-Ch infected cats at 100 mg/kg bid for 1 week followed by 200 mg/kg bid.

Figure 4:
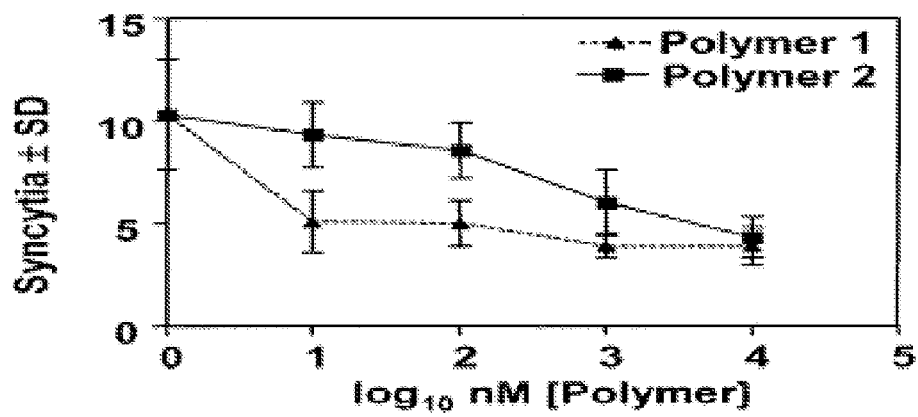
FIG. 4: Treatment effect of various doses of a polyphenol-quinonoid polymer according to the invention on HeLa-CD4/CCR5-expressing cells as described in Example 4. A: Number of syncytia formed in the cell monolayer of cells infected with HIV-1-SF162, when cells are pre-treated with "polymer 1" or "polymer 2" (control) prior to transduction with the pseudotyped virus; B: Luciferase activity in HeLa-CD4/CCR5-expressing cells transduced with pseudotyped virus expressing HIV-1-SF162 envelope protein when treated with "polymer 1" or "polymer 2" (control).
Figure 4:
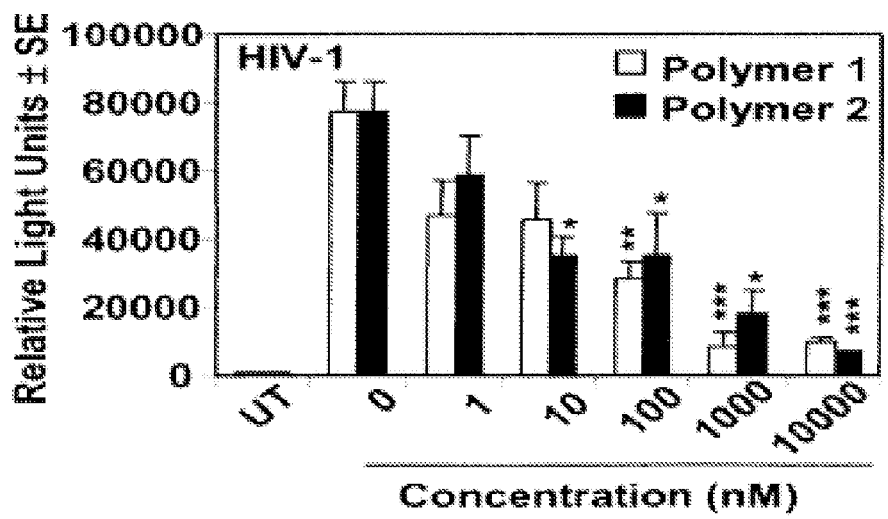
Figure 5:
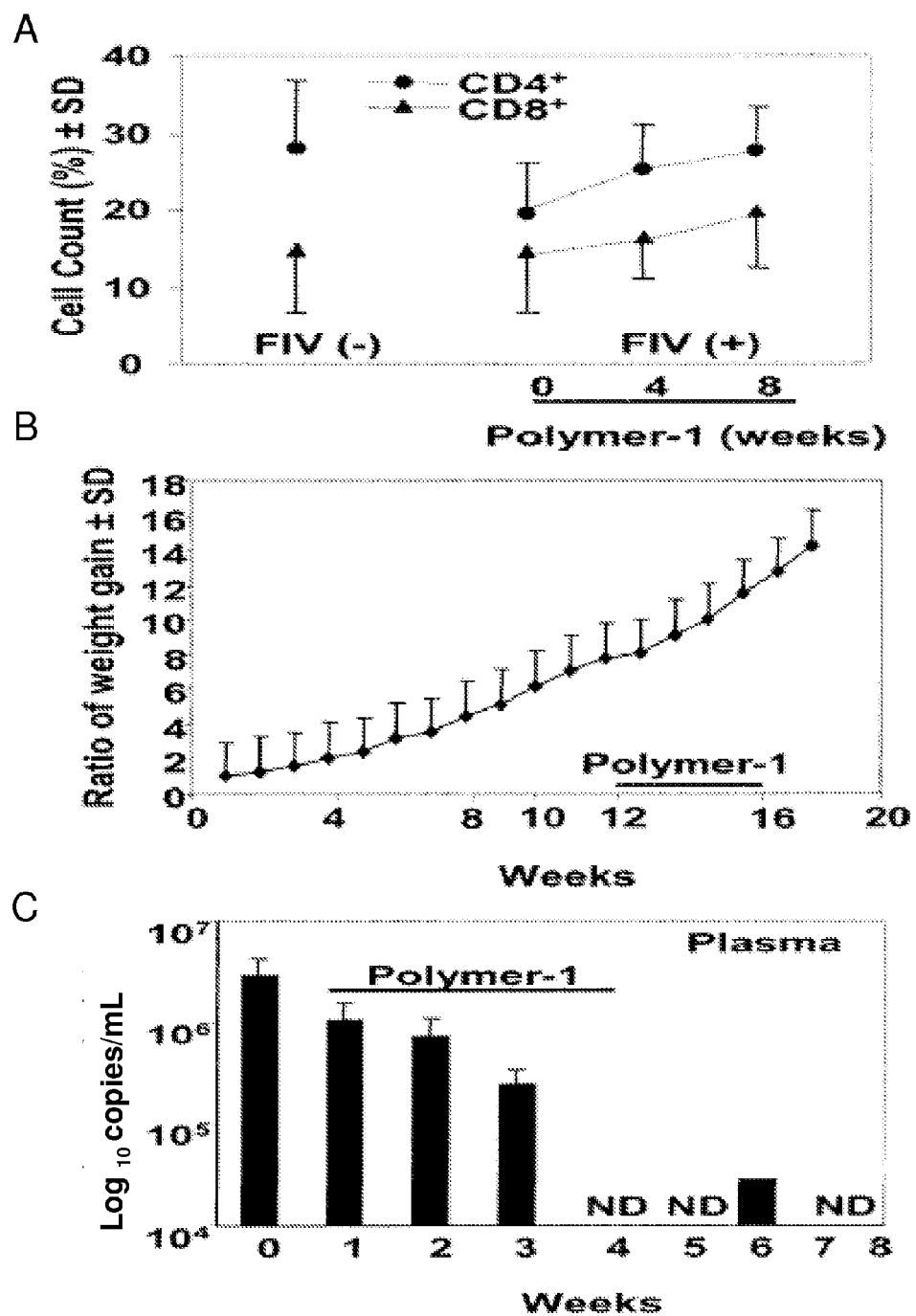
FIG. 5: Treatment effect of a polyphenol-quinonoid polymer according to the invention on FIV-1-induced viral pathogenesis in vivo as described in Example 5. A: $CD4^+$ and $CD8^+$ T cell counts by flow cytometry in FIV-infected animals (FIV (+)) (n=4) treated with "polymer 1" up to 8 weeks as compared to non-infected, non-treated healthy animals (FIV (−)); B: Ratio of weight gain, in FIV-infected animals treated with "polymer 1" showed over weeks of examination compared to FIV-infected but untreated animals (controls); C: Plasma viral load of FIV-infected animals and their polymer-treated counterparts. ND: not detectable.

Serial plasma levels were taken for evaluation of viral load together with PBMCs, which were analyzed for CD4$^+$ and CD8$^+$ T cell counts in blood as described below. Average CD4 T cell levels showed a reduction in FIV-infected animals, compared to matched uninfected healthy cats while CD8 T cell levels were similar in both FIV-infected and uninfected animals (FIG. 4A), as reported earlier for this model (Kennedy et al., 2004, above). In contrast, both CD4$^+$ and CD8$^+$ T cell counts in "polymer 1"-treated animals increased from week 12 onward (FIG. 5A). The improvement in CD4$^+$ and CD8$^+$ T cell levels persisted even after "polymer 1" treatment was stopped. All "polymer 1" treated animals continued to show consistent weight gain during the treatment (4 weeks) and wash out (9 weeks) periods (FIG. 5B).

At 12 weeks post-infection, prior to initiation of "polymer 1" treatment, the mean plasma viral load was 7.0±0.4 $\log_{10}$ copies/ml. After two weeks of "polymer-1" treatment, FIV-infected cats showed an average viral load of 5.3±1.3 $\log_{10}$ copies/ml. "Polymer-1"-treated animals exhibited undetectable viral RNA levels by week 4. This trend of viral suppression was maintained in the absence of any treatment for a subsequent 4 week period (FIG. 5C). Viral RNA was detected in some animals at week 6 but the viral load did not reach levels observed in the animals prior to the washout period (FIG. 5C).

These studies revealed a marked reduction in viral load over time to a point that was undetectable by 4 weeks post-treatment.

CD4+ and CD8+ T Cell Quantification

The quantification was performed by flow cytometry.

RNA Isolation and Reverse Transcription

Since, at various stages of the disease, plasma viral RNA load remains the most potent predictor of outcome in HIV-1-infected individuals, suppression of viral RNA is but a necessary feature of any therapeutic approach. Therefore, plasma viral RNA loads were measured at regular intervals throughout the experimental period to evaluate viral load changes in cats treated with or without "polymer 1" as follows. Plasma from animals treated for weeks 0, 1, 2, 3, 4 ("polymer 1" treatment) and 5, 6, 7 (wash-out period) were isolated from whole blood by centrifugation and stored at −80° C. Viral RNA was extracted using Trizol LS reagent (Invitrogen) according to manufacturer's instructions. RNA obtained was quantified using spectrophotometric analysis and subjected to complimentary DNA (cDNA) preparation. Five µg of RNA was used in a 50 µl total reaction. A real time reverse transcriptase (RT-PCR) protocol using primers, that detect the FIV pol gene from multiple strains was used to determine the number of copies of viral RNA/ml of plasma as previously described (Kennedy et al., 2004, above).

Statistical Analysis

Comparisons between groups for lymphocyte levels and viral loads were made using Welch's unpaired t-test. Statistical analyses were performed using Instat Graphpad 3.01 (San Diego, Calif., USA) and P values of less than 0.05 were considered significant.

Therefore, these data show that FIV-infected animals treated with "polymer-1" displayed a consistent rise in blood CD4$^+$ T cell levels, which was accompanied by a marked reduction of virus copy number in plasma to undetectable levels (p<0.05) that was maintained up to four weeks post-cessation of polymer-1 treatment. The suppression of viral replication ex vivo and in vivo mediated by the present polyphenol-quinonoid derivative according to the invention supports the use of polyphenol-quinonoid derivatives according to the invention as therapeutics for HIV-1-infection, as predicted by the above molecular modeling studies.

All together, these results supports that polyphenol-quinonoid derivatives according to the invention are able to suppress HIV-1 and FIV replication and infectivity through inhibition of RT, while improving CD4$^+$ and CD8$^+$ lymphocyte counts of infected animals together with reducing plasma viral levels and leading in substantial weight gain. Further, $IC_{50}$ values to achieve inhibition of viral RT, as well as blocking of replication, are at least lower by a magnitude of 4 log doses, which underscores the relative safety of the polyphenol-quinonoid polymers and their potential for clinical evaluation. Further, considerably low cost of synthesis and storage of those polymers, are a further advantage of their use in anti-HIV-1 therapies.

Example 6

Effect of Polyphenol-Quinonoid Polymer Derivatives According to the Invention on Bacterial Organisms The polymer mixture according to the invention obtained as described under Example 1 was tested for its antimicrobial efficacy against a range of bacterial Gram positive and Gram negative organisms: *Escherichia coli*, *Bacillus subtilis*, *Pseudomonas aerginosa*, and *Pseudomonas ptudia*. A minimum inhibitory concentration (MIC) assay (followed as described previously in Mouton, J. W. and Vinks, A. A., (2005) *Clinical Pharmacokinetics*, Volume 44, Number 2, pp. 201-210) was used initially to test for possible antimicrobial activity. The polymer mixture was tested at concentrations ranging from 10 mg/ml to 0.1 mg/ml. MIC value are presented in Table 2 below.

TABLE 2

| | MIC Value (mg/ml) | | | |
|---|---|---|---|---|
| | B. subtilis | E. coli | P. aerginosa | P. ptudia |
| Polymer Mixture of Example 1 | <0.1 | <0.1 | ~0.1 | ~0.1 |

Those results show that polymer mixtures according to the invention are inhibitory against all organisms at the low end of the concentrations tested.

The inhibitory action of the polymer mixtures according to the invention was further investigated to determine if the action is bacteriocidal or bacteriostatic. *P. aerginosa* was selected as the test organism using test concentrations of a polymer mixture according to the invention obtained as described in Example 1 from 2.5 mg/ml to 0.1 mg/ml. At 2.5 mg/ml, the outgrowth of *P. aerginosa* was prevented while at 0.5 mg/ml recovery of viable cells was possible. It appears that the polymer mixtures according to the invention are bacteriocidal at concentrations near 2.5 mg/ml.

Example 7

Exposition of Textile and Biological Tissue with Polyphenol-Quinonoid Polymer Derivatives According to the Invention Antibacterial action on textiles can be followed by the American Association of Textile Chemists and Colorists (AATCC) protocols as described by Hee et al., 2001, *Textile Research Journal*, 71(4), 318-323 and by Sun, 2005, *J. Chem. Educ.*, 82, 60-64.

The invention claimed is:

1. A method of treating or repressing a disease or disorder caused by a retrovirus infection, said method comprising orally administering to a subject in need thereof a therapeutically effective amount of a composition comprising a mixture of polyphenol-quinonoid polymer derivatives according to Formula (I):
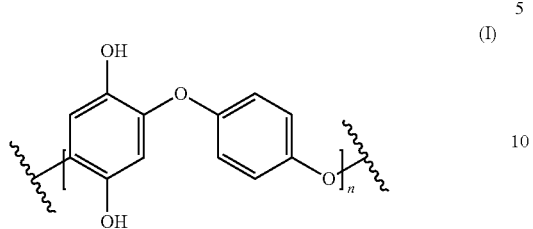
(I)
wherein n is an integer selected from 1 and 2, pharmaceutically acceptable salts or pro-drugs thereof or a pharmaceutical formulation of said composition, wherein the retrovirus is HIV-1.
* * * * *